United States Patent [19]

Fried

[11] Patent Number: 5,179,218
[45] Date of Patent: Jan. 12, 1993

[54] PROCESS FOR THE OXIDATION OF ALCOHOLS TO ACIDS

[75] Inventor: Herbert E. Fried, Houston, Tex.

[73] Assignee: Shell Oil Company, Houston, Tex.

[21] Appl. No.: 769,080

[22] Filed: Sep. 30, 1991

[51] Int. Cl.$^5$ .............................................. C07C 51/16
[52] U.S. Cl. ............................... 554/134; 554/132; 554/139; 554/159; 562/512.2; 562/523; 562/538; 562/540
[58] Field of Search ............... 260/413; 562/538, 537, 562/540, 587, 523, 512.2; 554/132, 134, 139, 159

[56] References Cited

U.S. PATENT DOCUMENTS 4,620,033 10/1986 Isshiki et al. ..................... 562/519

FOREIGN PATENT DOCUMENTS 5096516 11/1986 Japan .

OTHER PUBLICATIONS

Chemical Abstracts, vol. 69, #25, p. 990 105 836c.
Miyazawa et al., "Oxidation of Benzyl Alcohol with Iron(III) Using Polymers Containing Nitroxyl Radical Structure as a Mediator", J. Polym. Sci., Polym. Chem. Ed., 23(9), 1985, pp. 2487-2494.
Grigo ev et al., "Participation of Nitroxyl Radical in the Oxidation of Aldehyde and Alcohol Groups in 3-Imidazolin-1-Oxyls", Izc. AKad. Nauk SSSR, Ser. Khim., (1), 1978, pp. 208-210.
Miyzawa et al., "Oxidation of Benzyl Alcohol with Copper(II) Mediated by a Polymeric Oxoaminium Salt", J. Mol. Catal., 49(1), 1988, 131-134.
Ganem et al., "Biological Spin Labels as Organic Reagents, Oxidation of Alcohols to Carbonyl Compounds Using Nitroxyls", J. Org. Chem., 40(13), 1975, pp. 1998-2000.
Miyazawa et al., "Oxidation of Benzyl Alcohol by Iron-(III) Mediated by Nitroxyl Radical", J. Mol. Catal., 31(2), 1985, pp. 217-220.
Anelli et al., "Fast and Selective Oxidation of Primary Alcohols to Aldehydes or to Carboxylic Acids and of Secondary Alcohols to Ketones Mediated by Oxoammonium Salts Under Two-Phase Conditions", J. Org. Chem., 52 (12), pp. 2559-2562, 1952.
Inokuchi et al., "A Selective and Efficient Method for Alcohol Oxidations Mediated by N-Oxoammonium Salts in Combination with Sodium Bromite", J. Org. Chem., 1990, 55, pp. 462-466.
Organic Synthesis, vol. 69, p. 212 (1990).
Semmelhack et al., "Oxidation of Alcohols to Aldehydes and Oxygen and Cupric Ion, Medicated by Nitrosonium Ion", J. Am. Chem. Soc. 1984, 106, 3374-3376.
Yamaguchi et al., "Application of Redox System Based on Nitroxides to Organic Synthesis", Pure & Applied Chemistry, vol. 62(2), 1990, pp. 217-222.

*Primary Examiner*—José G. Dees
*Assistant Examiner*—Deborah D. Carr
*Attorney, Agent, or Firm*—Pamela J. McCollough

[57] ABSTRACT

A process for the preparation of an alkanoic acid which comprises reacting the corresponding alkanol with a solubilized stable free radical nitroxide having the formula:

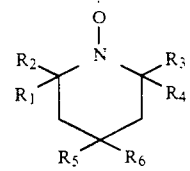

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid, and a bromide ion-containing compound in the presence of an oxidant at a temperature in the range of from about 25° C. to about 60° C., and thereafter separating out the alkanoic acid.

16 Claims, No Drawings

5,179,218

PROCESS FOR THE OXIDATION OF ALCOHOLS TO ACIDS

FIELD OF THE INVENTION

This invention relates to a process for the preparation of alkanoic acids by the oxidation of the corresponding alkanols in the presence of a stable free radical nitroxide, nitric acid, a bromide ion-containing compound and an oxidant.

BACKGROUND OF THE INVENTION

It is known to use nitroxyl radicals/oxoammonium salts in the oxidation of primary alcohols to produce aldehydes and acids and secondary alcohols to ketones (*Journal of Organic Chemistry*, vol. 52 (12), pp. 2559-2562 and *Journal of Organic Chemistry*, vol. 55, 1990, pp. 462-466). The primary products produced in these processes are aldehydes.

It is reported in the open literature that primary aliphatic alcohols can be converted to aldehydes in 30-40% yields in the presence of oxyl, and atmospheric oxygen (*Journal of American Chemical Society*, 1984, 106, pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217-222).

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.-270° C.

OBJECTS OF THE INVENTION

It is an object of this invention to produce alkanoic acids in high yields and with high selectivities from alkanols without producing large amounts of other products such as aldehydes and esters.

It has been found that in the oxidation of alkanols to alkanoic acids, dramatically increased reaction rates and higher yields of alkanoic acids can be obtained when catalytic amounts of a bromide ion-containing compound are utilized along with catalytic amounts of a stable free radical nitroxide, nitric acid and an oxidant.

SUMMARY OF THE INVENTION

This invention relates to a process for the preparation of an alkanoic acid which comprises reacting the corresponding alkanol with a solubilized stable free radical nitroxide having the formula:

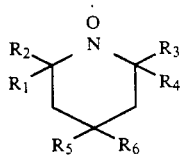

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid and a bromide ion-containing compound in the presence of an oxidant at a temperature in the range of from about 25° C. to about 60° C., and thereafter separating out the alkanoic acid.

DESCRIPTION OF THE PREFERRED EMBODIMENTS

The present process converts alkanols to the corresponding alkanoic acids by contacting the alkanol with a solubilized stable free radical nitroxide, nitric acid and a bromide ion-containing compound in the presence of an oxidant at a temperature in the range of from about 25° C. to about 60° C.

The alkanol reactant suitably comprises one or more alkanols having a carbon number in the range of from about 6 to about 30. An alkanol consisting essentially of primary, mono-alkanols is preferred. Most preferably, the alkanol reactant consists essentially of one or more $C_6$ to $C_{30}$ primary mono-alkanols. Preference can also be expressed for alkanols having from 8 to about 20 carbon atoms, with $C_9$ to $C_{18}$ alkanols considered more preferred and $C_{11}$ to $C_{18}$ alkanols considered most preferred. As a general rule, the carbon chains of the alkanols may be of either branched or linear (straight-chain) structure, although preference further exists for alkanol reactants in which greater than about 50 percent, more preferably greater than about 70 percent and most preferably greater than about 90 percent of the molecules are of linear (straight-chain) carbon structure. In large part, such preferences relate more to the utility and value of the products than to the operability or performance of the process of the invention.

The general suitability of such alcohols as reactants in oxidation reactions is well recognized in the art. Examples of specific alkanols and of commercially available alkanols and alkanol mixtures within this class are also well known. Commercially available mixtures of primary mono-alkanols prepared via the oligomerization of ethylene and the hydroformylation or oxidation and hydrolysis of the resulting higher olefins are particularly preferred.

Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620)., the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkanols to the corresponding acids. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

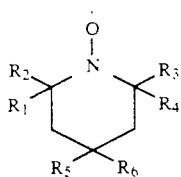

wherein each of $R_1$, $R_2$, $R_3$ and $R_4$ is an alkyl, aryl or heteroatom substituted alkyl group having 1 to about 15 carbon atoms and no hydrogen is bound to the remaining valences on the carbon atoms bound to the nitrogen, and each of $R_5$ and $R_6$ is alkyl, hydrogen, aryl or a substituted heteroatom. As used herein, the term "alkyl" is meant to include cycloalkyl. The alkyl (or heteroatom substituted) groups $R_1$-$R_4$ may be the same or different, and preferably contain 1 to 15 carbon atoms. Preferably, $R_1$-$R_4$ are methyl, ethyl, or propyl groups. In addition to hydrogen, the heteroatom substituents may include, halogen, oxygen, nitrogen and the like. Preferably, one of $R_5$ and $R_6$ is hydrogen with the other one being a substituted heteroatom which does not interfere with the reaction. Suitable substituted heteroatoms include

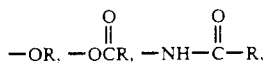

—NMe$_3$Cl$^-$, —O—SO$_3$H, —O—polymer and the like.

In a preferred embodiment, the nitroxide is selected from the group consisting of 2,2,6,6-tetramethyl-piperidine-1-oxyl, 4-hydroxy-2,2,6,-6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof, with 2,2,6,6-tetramethyl-piperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

As used herein, "nitric acid" refers to nitric acid, fuming nitric acid, or nitrous acid generated by contacting alkali metal nitrite with mineral acid. The nitric acid suitable for use in the present invention typically has a concentration in the range of from about 50 percent to about 100 percent, preferably about 70 percent. Generally, an amount of nitric acid in the range of from about 5 mole percent to about 100 mole percent, basis the number of moles of starting alkanol is used. If excess nitric acid is used and the reaction mixture becomes too acidic, the reaction stops. The nitric acid is typically added to the reaction mixture after all of the other reactants have been added. While not wishing to be bound by any particular theory, it is believed that nitrogen oxides (NO$_x$) are generated in the reaction and are the active species in the reaction.

The bromide ion-containing compound in the present invention can be any ionic bromide which is in a soluble form. The presence of bromide ion is critical to the instant process as it dramatically increases the rate of the reaction. In addition, the bromide ion stabilizes the nitroxide so that deoxygenation to the corresponding secondary amine is substantially minimized. As a result, less nitroxide can be used to achieve the desired conversions. The bromide ion is suitably introduced into the process as a quaternary alkyl bromide such as, for example, ammonium bromide, a tetraalkyl ammonium bromide such as, for example, tetramethyl ammonium bromide, an alkali metal bromide such as for example, sodium bromide, potassium bromide, lithium bromide, calcium bromide and the like. In a preferred embodiment, the bromide ion-containing compound is selected from the group consisting of ammonium bromide, sodium bromide, potassium bromide and mixtures thereof, with potassium bromide being particularly preferred.

The oxidants suitable for use in the instant invention are those compounds which, in the presence of nitric acid, are capable of oxidizing the stable free radical nitroxide to the oxoammonium salt. Suitable oxidants include oxygen or an oxygen-containing gas such as air. Whereas pure oxygen is preferred to accomplish the desired conversion, the oxygen can also be diluted with an inert gas such as nitrogen, helium, argon or other similar gas. While air can be used as the oxidant, the reaction rate is much slower. For purposes of increasing the reaction rate, higher O$_2$ pressures such as, for example, 1000 psi can be utilized. In a preferred embodiment, pure oxygen is used as the oxidant and it is bubbled into the reaction solution at atmospheric pressure. It is critical that the flow of the oxidant or oxygen-containing gas be continuous throughout the process in order to keep the reaction going. If the flow of oxygen is stopped during the course of the reaction, the reaction rate is significantly reduced.

The reaction in the instant invention can be carried out in the presence or absence of a solvent. When the reaction is carried out in the presence of a solvent, the solvent is generally a solvent in which the alkanol is readily soluble. Solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of acetonitrile, ethyl acetate, tertiary alcohols such as tertiary butyl alcohol, dichloromethane, chlorobenzene, carbon tetrachloride, chloroform, dichloroethylene and mixtures thereof. In a preferred embodiment, the solvent is selected from tertiary butyl alcohol and dichloromethane. The amount of solvent utilized in the process is typically in the range of from about 20:1 to about 0.5:1, preferably from about 10:1 to about 5:1, basis the weight of the starting alkanol.

The amounts and concentrations of the reactants utilized in the process of the instant invention can vary within wide ranges. The amount of stable free radical nitroxide is typically in the range of from about 1 mole percent to about 50 mole percent, preferably from about 5 mole percent to about 30 mole percent, basis the number of moles of starting alkanol. Generally, the amount of nitric acid utilized will be in the range of from about 5 mole percent to about 100 mole percent, preferably from about 25 mole percent to about 50 mole percent, basis the starting alkanol. Generally, the bromide ion-containing compound is present in an amount sufficient to catalyze the reaction. Typically, the amount of bromide ion-containing compound is about 6 mole percent, basis the starting alkanol.

The process of the present invention is typically conducted under mild conditions, with good results being obtained using a temperature in the range of from about 25° C. to about 60° C., preferably about 30° C. to about 45° C., and more preferably about 35° C. to about 40° C. Reaction pressures are not critical although higher pressures result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized, the solvent utilized, and on the concentration of the nitroxide.

The process of the instant invention can be carried out in a variety of ways. For example, 0.032 moles of alkanol, 0.006 moles percent by weight of the nitroxide, and 0.002 moles of bromide ion-containing compound may be added to the reaction vessel, followed by the addition of 0.016 moles of nitric acid and $O_2$. Alternatively, the alkanol, the nitroxide, the nitric acid, and the bromide ion-containing compound and the oxidant may be added simultaneously to the reaction vessel and allowed to reach equilibrium. In a preferred embodiment, the reaction is carried out by adding the alkanol, the nitroxide, and the solubilized bromide ion-containing compound together with the solvent, if one is used, and thereafter adding the nitric acid and bubbling an oxidizing gas through the mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. The reaction product can be purified by a number of conventional means such as, for example, distillation or by other means known to those skilled in the art.

Depending upon process conditions and the nitroxide used, the yields of alkanoic acid obtained by this invention are at least about 80% of starting alkanol material being converted. The products produced by the instant process can be used in a variety of applications. For example, these products can be used as soaps, detergents, and plasticizers, or as intermediates to produce esters or amides.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

Example 1

6 Grams of 1-dodecanol, 1 gram of 2,2,6,6-tetramethyl-piperidine-1-oxyl, 25 milliliters of tertiary butyl alcohol, and 0.25 grams of potassium bromide dissolved in 1 gram of water were charged to a 100 milliliter round bottomed flask. To this mixture was added 1 gram of 70% nitric acid. An 02 steam was then bubbled through the mixture at atmosphereic pressure. The reaction was held at a temperature of 35° C. over a 2 hour period. The results are presented in Table I.

Example 2

6 Grams of 1-dodecanol, 1 gram of 2,2,6,6-tetramethyl-piperidine-1-oxyl, 25 milliliters of dichloromethane, and 0.25 grams of potassium bromide dissolved in 1 gram of water were charged to a 100 milliliter round bottomed flask. To this mixture was added 1 gram of 70% nitric acid. An and $O_2$ steam was then bubbled through the mixture at atmospheric pressure. The reaction was held at 35° C. over a 4 hour period. The results are presented in Table I.

Example 3

6 Grams of 1-dodecanol, 0.5 grams of 2,2,6,6-tetramethyl-piperidine-1-oxyl, 25 milliliters of dichloromethane, and 0.25 grams of potassium bromide dissolved in 1 gram of water were charged to a 100 milliliter round bottomed flask. To this mixture was added 1 gram of 70% nitric acid. An $O_2$ stream was then bubbled through the mixture at atmospheric pressure. The reaction was held at a temperature of 35° C. over a 4 hour period. The results are presented in Table I.

Example 4

6 Grams of 1-dodecanol, 1 gram of 2,2,6,6-tetramethyl-piperidine-1-oxyl, 25 milliliters of dichloromethane and 0.25 grams of potassium bromide dissolved in 1 gram of water were charged to a 100 milliliter round bottomed flask. To this mixture was added 1 gram of 70% nitric acid. An $O_2$ stream was then bubbled through the mixture at atmospheric pressure. The reaction was held at a temperature of 45° C. over a 4 hour period. The results are presented in Table I.

Comparative Example A

Comparative Example A was carried out in a manner similar to Example 1 except that no bromide ion-containing compound was used and the reaction was carried out over a four hour period. The results are presented in Table I.

Comparative Example B

Comparative Example B was carried out in a manner similar to Example 2 except that no bromide ion-containing compound was used. The results are presented in Table I.

Comparative Example C

Comparative Example C was carried out in a manner similar to Example 1 except that no nitroxide was used. The results are presented in Table I.

As can be seen in Table I, the bromide ion-containing compound dramatically accelerates the reaction rates and results in improved yields. In addition, it can also be seen that the nitroxide is essential for the oxidation of alcohols to acids.

TABLE I

Oxidation Of Alkanols to Acids

|  | % Conversion | % Sel. Acids | % Sel. Esters + Heavies | % Sel. Aldehydes |
| --- | --- | --- | --- | --- |
| Example 1 | 96 | 86 | 8 | 6 |
| Example 2 | >99.9 | 90 | 7 | 3 |
| Example 3 | 98 | 82 | 10 | 8 |
| Example 4 | 99 | 89 | 7 | 4 |
| Comparative Example A | 54 | 73 | 22 | 5 |
| Comparative Example B | 65 | 5 | 37 | 58 |
| Comparative Example C | 0 | 0 | 0 | 0 |

What is claimed is:

1. A process for the preparation of an alkanoic acid which comprises reacting the corresponding alkanol with a solubilized stable free radical nitroxide having the formula:

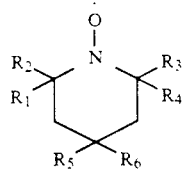

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, nitric acid, and a bromide ion-containing compound in the presence of an oxidant at a temperature in the range of from about 25° C. to about 60° C., and thereafter separating out the alkanoic acid.

2. The process of claim 1 wherein the solubilized stable free radical nitroxide is selected from the group consisting of 2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

3. The process of claim 2 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein the stable free radical nitroxide is dissolved in a solvent selected from the group consisting of acetonitrile, ethyl acetate, tertiary butyl alcohol, dichloromethane, chlorobenzene, carbon tetrachloride, chloroform, dichloroethylene and mixtures thereof.

5. The process of claim 4 wherein the stable free radical nitroxide is dissolved in a solvent selected from the group consisting of tertiary butyl alcohol, dichloromethane and mixtures thereof.

6. The process of claim 1 wherein the amount of nitric acid is in the range of from about 5 mole percent to about 100 mole percent, basis the starting alkanol.

7. The process of claim 1 wherein said bromide ion-containing compound is selected from the group consisting of a quaternary alkyl bromide, a tetraalkyl bromide, an alkali metal bromide and mixtures thereof.

8. The process of claim 7 wherein said bromide ion-containing compound is selected from the group consisting of ammonium, bromide, sodium bromide, potassium bromide and mixtures thereof.

9. The process of claim 1 wherein said alkanol is contacted with said solubilized stable free radical nitroxide and said bromide ion-containing compound, followed by the addition thereto of said nitric acid and said oxidant.

10. The process of claim 9 wherein the amount of solubilized stable free radical nitroxide is in the range of from about 1 mole percent to about 25 mole percent, basis the number of moles of the alkanol.

11. The process of claim 10 wherein the amount of solubilized stable free radical nitroxide is in the range of from about 5 mole percent to about 20 mole percent, basis the number of moles of the alkanol.

12. The process of claim 1 wherein said oxidant is an oxygen-containing gas.

13. The process of claim 12 wherein said oxygen containing gas is selected from the group consisting of pure oxygen and air.

14. The process of claim 13 wherein said oxygen-containing gas is pure oxygen.

15. The process of claim 1 wherein said process is carried out at a temperature in the range of from about 30° C. to about 45° C. and at atmospheric pressure.

16. The process of claim 15 wherein said process is carried out at a temperature in the range of from about 35° C. to about 40° C. and at atmospheric pressure.

* * * * *